United States Patent [19]

Podszun et al.

[11] Patent Number: 5,147,903
[45] Date of Patent: * Sep. 15, 1992

[54] DENTAL MATERIALS

[75] Inventors: Wolfgang Podszun, Cologne; Fritjof Bley, Achberg-Liebenweiler, both of Fed. Rep. of Germany

[73] Assignee: Bayer Aktiengesellschaft, Leverkusen, Fed. Rep. of Germany

[*] Notice: The portion of the term of this patent subsequent to Jun. 26, 2007 has been disclaimed.

[21] Appl. No.: 681,815

[22] Filed: Apr. 8, 1991

Related U.S. Application Data

[63] Continuation of Ser. No. 362,722, Jun. 7, 1989, abandoned.

[30] Foreign Application Priority Data

Jun. 16, 1988 [DE] Fed. Rep. of Germany ....... 3820498

[51] Int. Cl.$^5$ .................. C08F 265/04; A61C 13/00
[52] U.S. Cl. .................. 523/115; 523/116; 525/309
[58] Field of Search .......... 524/307, 308; 523/115, 523/116; 525/309

[56] References Cited

U.S. PATENT DOCUMENTS

| | | | |
|---|---|---|---|
| 4,396,377 | 8/1983 | Roemer et al. | 523/115 |
| 4,937,144 | 6/1990 | Podszun et al. | 523/115 |

*Primary Examiner*—John C. Bleutge
*Assistant Examiner*—Mark Sweet
*Attorney, Agent, or Firm*—Sprung Horn Kramer & Woods

[57] ABSTRACT

Dental materials contain a filler which consists of polymeric crosslinked (meth)-acrylates having a particle size in the range from 0.001 to 100 μm, a degree of swelling of 50 to 2,000% by weight and a degree of crosslinking of 1 to 100% by weight, (meth)-acrylic acid esters which form crosslinkages and no crosslinkages, and additives.

5 Claims, No Drawings

DENTAL MATERIALS

This is a continuation of application Ser. No. 362,722, filed Jun. 7, 1989 now abandoned.

The invention relates to dental materials, their preparation and their use.

Dental materials can be used, for example, for the production of false teeth, crowns, bridges, inlays, onlays, dental fillings and dental lacquers.

The preparation of dental materials based on polymeric (meth)-acrylates is known. Thus, for example, materials which contain polymethyl methacrylate bead polymers as the powder component and mixtures of methyl methacrylate and ethylene dimethacrylate are prepared; the mixtures in general harden by free radical polymerization, with shaping (Ullmann's Encyclopedia of Industrial Chemistry, Fifth Edition, Volume A8, p. 277 et seq. VCH Verlagsgesellschaft m.b.H., Weinheim 1987).

Dental materials which, in addition to non-crosslinked polymethyl methacrylate, contain a crosslinked polymethyl methacrylate in the form of a bead polymer as a filler are described in U.S. Pat. No. 4,396,374 to Roemer et. al. These materials are built up by the "interpenetrating plymer network" (IPN) principle. IPN systems are known (J. Polym. Science 12, 141 (1977), J. Polym. Science 16, 583 (1978)).

The materials known from this reference do not have adequate mechanical properties and cannot be processed in layers of any desired thickness (for example in dental lacquers).

Dental materials containing a) 5 to 35 parts by weight of a filer consisting of polymeric crosslinked (meth)-acrylates having a particle size in the range from 0.001 to 10 $\mu$m, a degree of swelling of 50 to 2,000% by weight and a degree of crosslinking of 1 to 100% by weight, in each case based on the polymer, b) 40 to 90 parts by weight of (meth)-acrylates which can form crosslinkages, c) 0 to 40 parts by weight of (meth)-acrylates which cannot form crosslinkages and d) 0.1 to 10 parts by weight of one or more additives, have been found.

Surprisingly, the dental materials according to the invention are distinguished by a marked hardness and rigidity. They can be processed to very thin layers.

(Meth)acrylates in the context of the present invention are esters of acrylic acid and/or of methacrylic acid. Esters of methacrylic acid are preferred.

Component (a)

Fillers in the context of the invention are polymeric crosslinked (meth)-acrylates having a particle size in the range from 0.001 to 100 $\mu$m, preferably 0,01–10 $\mu$m, a degree of swelling of 50 to 2,000% by weight and a degree of crosslinking of 1 to 100% by weight, in each case based on the polymer.

In the fillers, the poly(meth)acrylates according to the invention have a degree of crosslinking of 1 to 100% by weight, preferably 50 to 100% by weight.

The degree of crosslinking is defined here as the percentage (content) of methacrylic acid esters which can form crosslinkages based on the polymer.

Monomeric (meth)-acrylates, in the fillers, which form crosslinkages are (meth)-acrylates having 2 or more, preferably 2 to 4, polymerizable double bonds in the molecule.

Examples which may be mentioned of monomeric (meth)-acrylates which form crosslinkages are: ethylene glycol dimethacrylate, diethylene glycol dimethacrylate, triethylene glycol dimethacrylate, glycerol dimethacrylate, glycerol trimethacrylate, trimethylolpropane trimethacrylate, pentaerythritol dimethacrylate, pentaerythritol trimethacrylate, pentaerythritol tetramethacrylate, derivatives of bisphenol A, such as bisphenol A dimethacrylate and bisphenol A diglycidyl dimethacrylate, urethane methacrylates which can be prepared by reaction of diisocyanates and hydroxyalkyl methacrylates, such as $$CH_2=C(CH_3)-C(O)-O-CH_2-CH_2-O-C(O)-NH-CH_2-CH_2-CH_2-CH_2-CH_2-NH-C(O)-O-CH_2-CH_2-O-C(O)-C(CH_3)=CH_2$$

and reaction products of polyols, dissocyanates and hydroxyalkyl methactrylates (DE-A 3,703,080, DE-A 3,703,130 and DE-A 3,703,120), such as, for example, $$CH_3-CH_2-C[CH_2-O-C(O)-N(H)-CH_2-CH_2-CH_2-CH_2-CH_2-CH_2-N(H)-C(O)-O-CH(CH_2-O-C(O)-C(CH_3)=CH_2)(CH_2-O-C(O)-C(CH_3)=CH_2)]_3$$

Monomeric (meth)-acrylates which form crosslinkages, such as ethylene glycol dimethacrylate, diethylene glycol dimethacrylate, triethlene glycol dimethacrlate and glycerol dimethacrylate, are preferred.

Examples which may be mentioned of monomeric (meth)-acrylates, in the fillers, which do not form crosslinkages are $C_1-C_{12}$-, preferably $C_1-C_4$-alkyl methacrylates, such as methyl methacrylate, ethyl methacrylate, n-propyl methacrylate, isopropyl methacrylate, n-butyl methacrylate and t-butyl methacrylate, hydroxyalkyl ($C_1-C_4$) methacrylates, such as 2-hydroxyethyl methacrylate, 2-hydroxypropyl methacrylate, diethylene glycol monomethacrylate and triethylene glycol monomethacrylate, and alkoxy ($C_1-C_4$)ethyl methacrylates, such as 2-methoxyethyl methacrylate, 3-methoxybutyl methacrylate and ethyltriglycol methacrylate.

Examples of preferred monomeric (meth)-acrylates which do not form crosslinkages are methyl methacrylate, ethyl methacrylate and 2-hydroxyethyl methacrylate.

The monomeric (meth)-acrylates are known per se and can be prepared, for example, by reaction of (meth)acrylyl chloride with the corresponding alcohols.

It is of course possible for the (meth)-acrylates according to the invention in the fillers to form copolymers with other monomers. Examples which may be mentioned here are copolymers with styrene, α-methylstyrene, acrylonitrile and vinyl acetate. In these cases, the content of the comonomer is 0 to 40, preferably 0 to 20% by weight, based on the polymer.

The degree of swelling is understood as the uptake capacity of the poly(meth)acryaltes according to the invention for liquid. The degree of swelling is measured by the uptake capacity for tetrahydrofuran at 20° C. The poly(meth)acryaltes according to the invention have a swelling capacity of 50 to 2,000% by weight, preferably 100 to 1,000% by weight, based on the polymer.

The fillers according to the invention in general have an average particle diameter of 0.001 to 100 μm, preferably 0.01 to 10 μm.

The fillers according to the invention preferably have a gel content of 5 to 100% by weight, preferably 95 to 100% by weight, based on the polymer. In the context of the present invention, the gel content is understood, according to the invention, as the content of the polymer which is insoluble in tetrahydrofuran as the solvent at 20° C. The gel content is a parameter of the crosslinking which has actually occurred.

The fillers according to the invention preferably have an active surface area of 20 to 600 m$^2$/g, preferably of 50 to 300 m$^2$/g, measured by the BET method.

Fillers according to the invention having a particle a size of about 5-100 μm can be synthesized by the suspension polymerization process.

Preferred fillers according to the invention having a particle size of 0.001 to 10 μm can be prepared by polymerizing, as monomers, (meth)-acrylates which form crosslinkages and if appropriate (meth)-acrylates which do not form crosslinkages, and if appropriate further commoners, in the presence of an organic solvent with a solubility parameter of 8 to 15 [cal$^{0.5}$ cm$^{-1.5}$], the monomer content of (meth)-acrylates which form crosslinkages being 50 to 100% by weight.

Organic solvents can be defined by the so-called solubility parameter (H. G. Elias, Makromoleküle, pages 192-196 (1981)). Solvents having a parameter of 8 to 15 [cal$^{0.5}$ cm$^{-1.5}$], preferably 8.5 to 12 [cal$^{0.5}$ cm$^{-1.5}$], are used for the process according to the invention.

The following solvents may be mentioned as examples: amyl acetate, tetrachloroethane, toluene, ethyl acetate, tetrahydrofuran, benzene, chloroform, methylene chloride, methyl chloride, acetone, butan-2-one and tert.-butanol.

The ratio of the amounts of solvent to monomeric (meth)-acrylates is in the range from 1:1 to 1:100, preferably 1:2 to 1:20.

The polymerization process according to the invention is in general carried out in the temperature range from 50° to 250° C., preferably 60 to 150° C. This polymerization can be carried out continuously or discontinuously.

The polymerization is in general carried out in the presence of initiators, such as sensitizers or agents which form free radicals.

The initiators are in general employed in an amount of 0.01 to 3% by weight, preferably 0.1 to 1.5% by weight, based on the total monomer.

Polymerization initiators which can be used are, for example, per-compounds, or azo compounds which supply free radicals. Example which may be mentioned are aliphatic azodicarboxylic acid derivatives, such as azobisisobutyronitrile or azodicarboxylic acid esters, peroxides, such as lauroyl peroxide, succinyl peroxide, dibenzoyl peroxide, oxide, p-chlorobenzoyl peroxide, 2,4-dichlorobenzoyl peroxide and peroxides such as methyl ethyl ketone peroxide, methyl isobutyl ketone peroxide, cyclohexanone peroxide and acetylacetone peroxide, alkyl esters of peracids, such as tert.-butyl peripivalate, tert.-butyl peroctoate, tert.-butyl perbenzoate, tert.-butyl perisononate, mono-tert.-butyl permaleate and tert.-butyl peracetate, percarbonates, such as dicyclohexyl and disopropyl percarbonate, dialkyl peroxides, such as di-tert.-butyl peroxide and dicumyl peroxide, hydroperoxides, such as tert.-butyl or cumene hydroperoxide, isophthalic mono-peracid or acetylcyclohexanesulphonyl peroxide.

A suspension of the filler is in general formed in the polymerization according to the invention. The filler can be isolated, for example, by evaporation of the solvent, for example in a spray drying process.

Component(b)

(Meth)-acrylic acid esters which can form crosslinkages in general contain two or more polymerizable active groups, for example double bonds or isocyanate groups, in the molecule. Esters of (meth)-acrylic acid with 2- to 5-hydric alcohols having 2 to 30 carbon atoms may be mentioned as preferred. Epoxide methacrylates and urethane methacrylates are particularly preferred.

(Meth)-acrylic acid esters of the formula

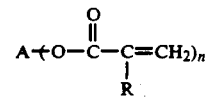

in which
A denotes a straight-line chain, branched or cyclic, aliphatic, aromatic or mixed aliphatic-aromatic radical having 2 to 25 C atoms which can be interrupted by —O— or NH bridges and substituted by hydroxyl, oxy, carboxyl, amino or halogen,
R denotes H or methyl and
n stands for an integer from 2 to 8, preferably 2 to 4, may be mentioned as examples.

Compounds of the following formulae may be mentioned as preferred:

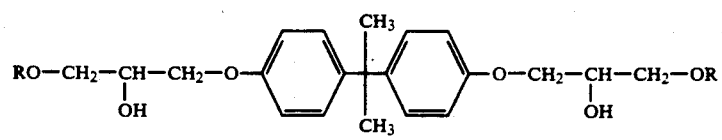

-continued
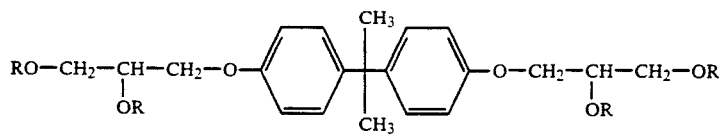
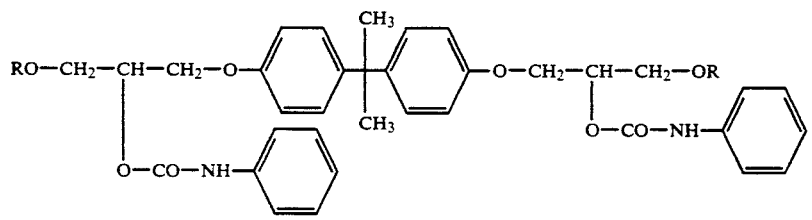
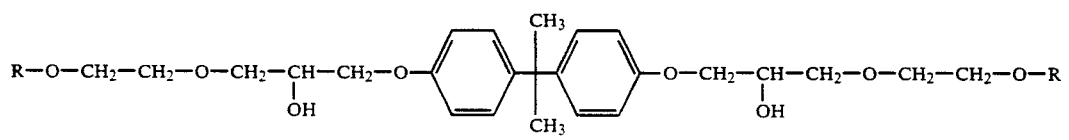
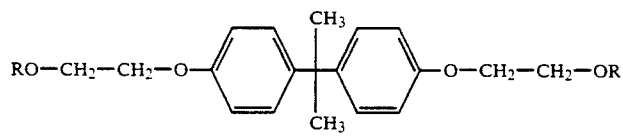
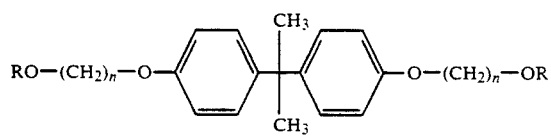
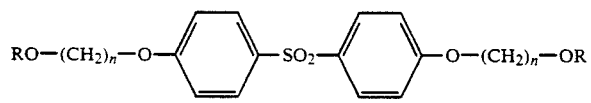
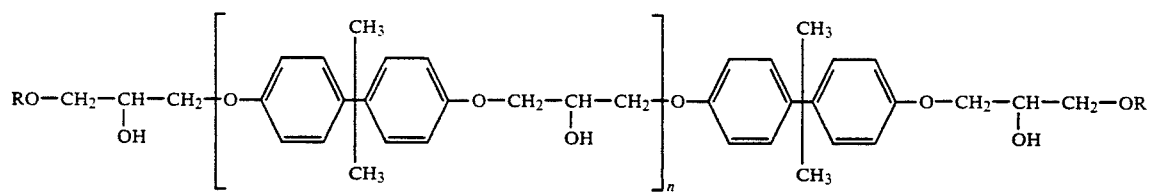
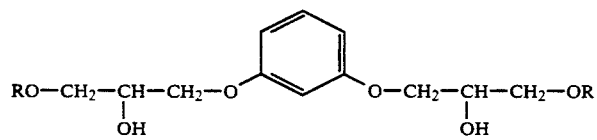
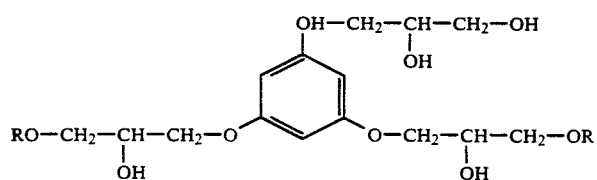

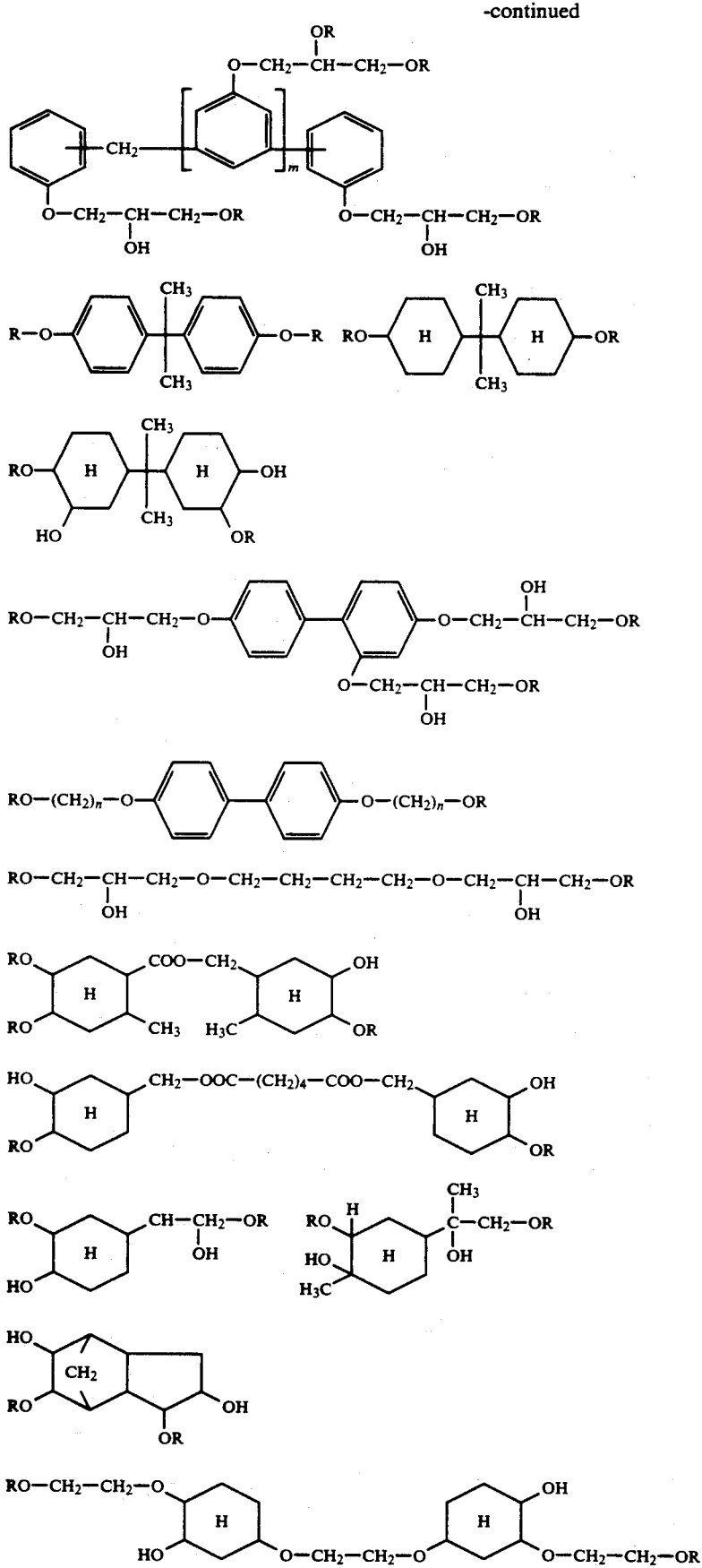

-continued
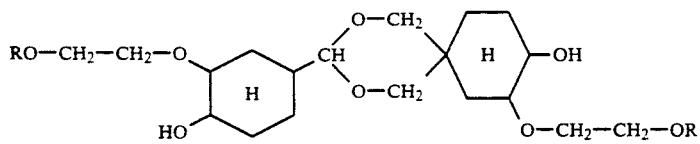
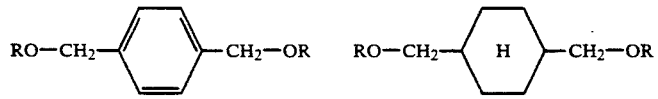
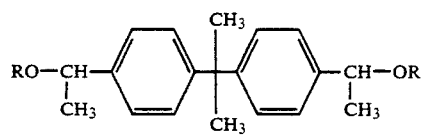
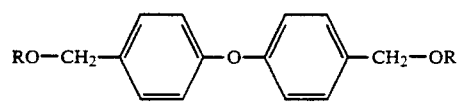
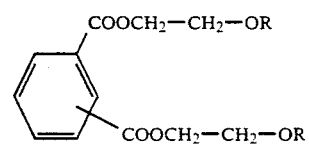
in the ortho, meta or para form
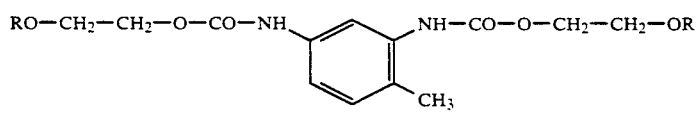
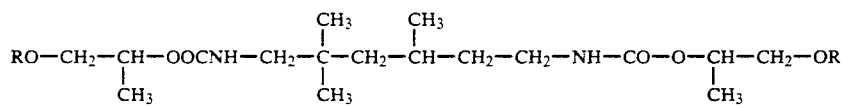
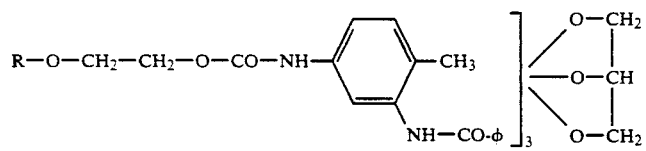
wherein
R stands for
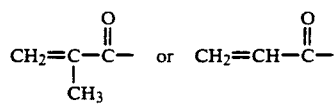
n denotes a number from 1 to 4 and
m denotes a number from 0 to 5.
Derivatives of tricyclodecane (EP-A 0,023,686) and reaction products of polyols, diisocyanates and hydroxyalkyl methacrylates (DE-A 3,703,120, DE-A 3,703,080 and DE-A 3,703,130) may also be mentioned. The following monomers may be mentioned as examples:
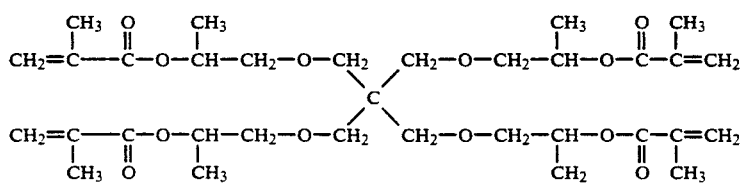

-continued
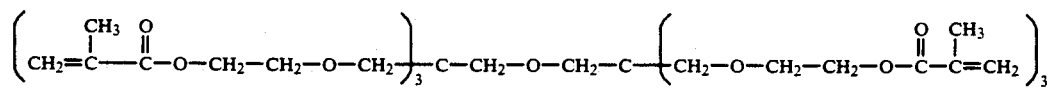
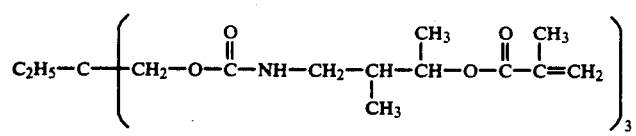
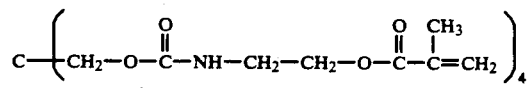
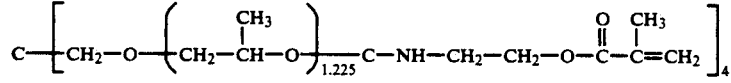
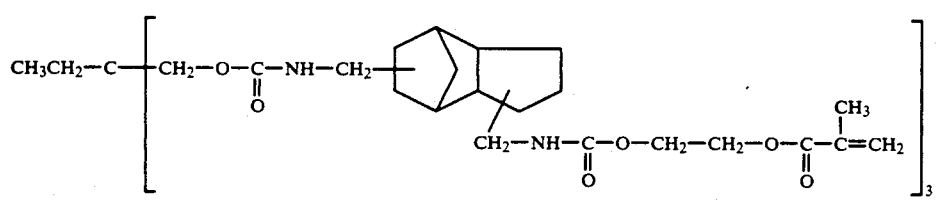
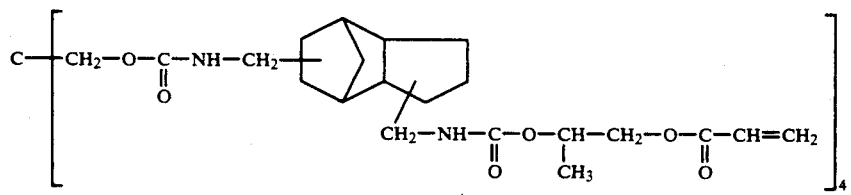
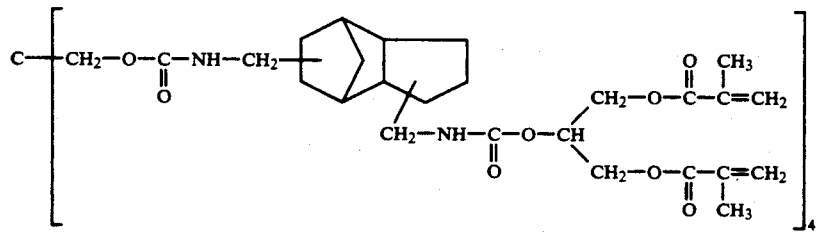
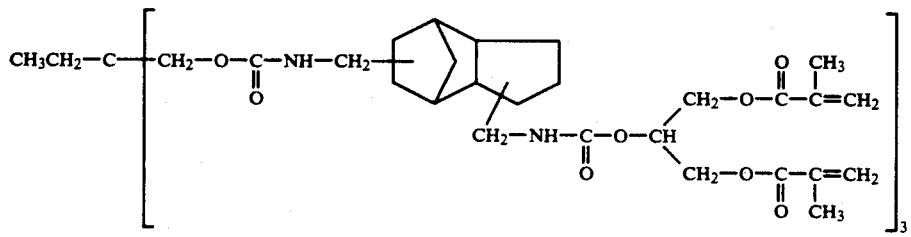

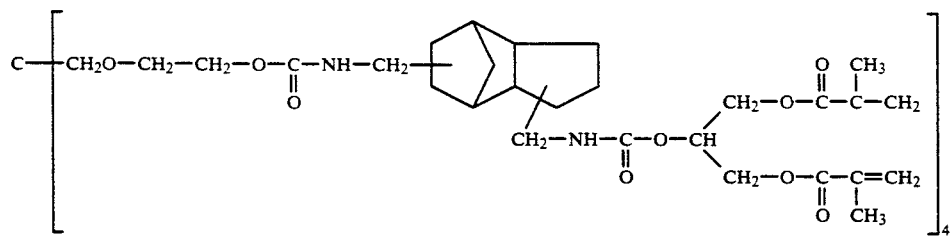
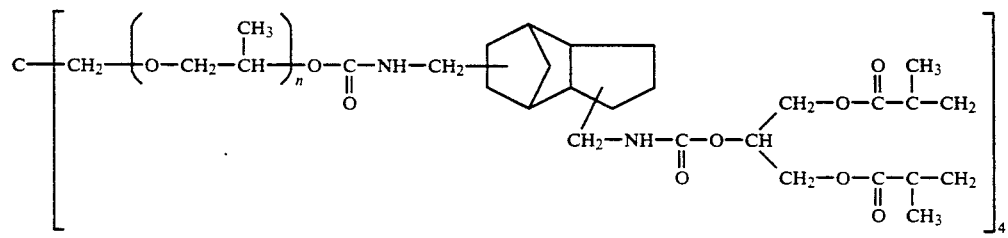
n = 1.225 (statistical mean value for 4 chains)
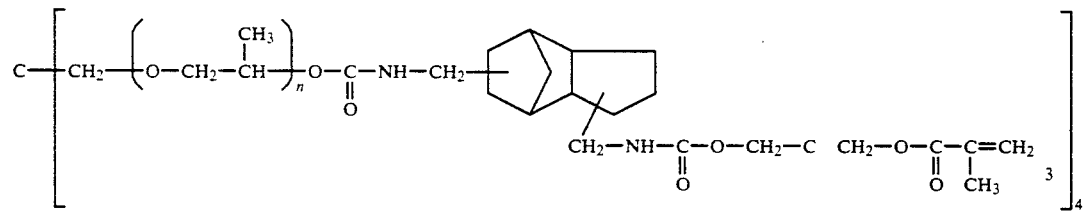
n = 1.225 (mean value)
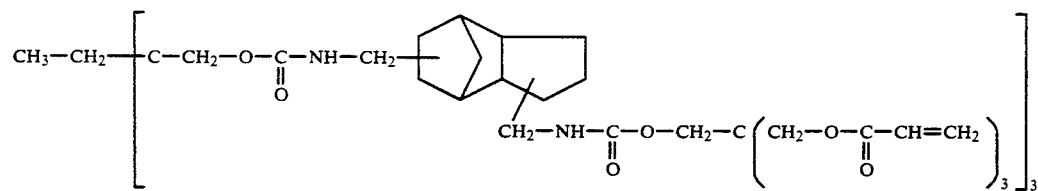
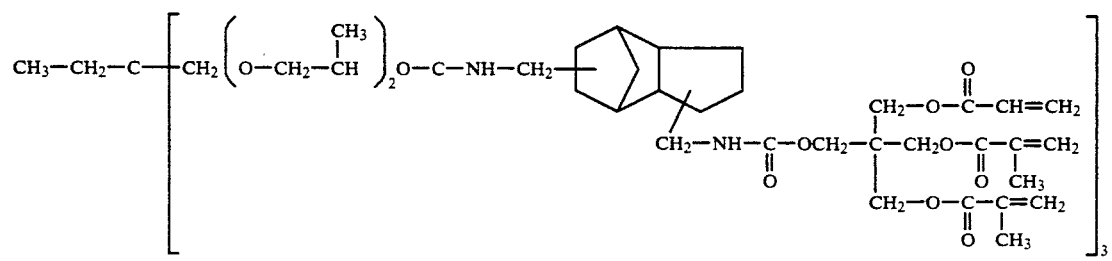

-continued
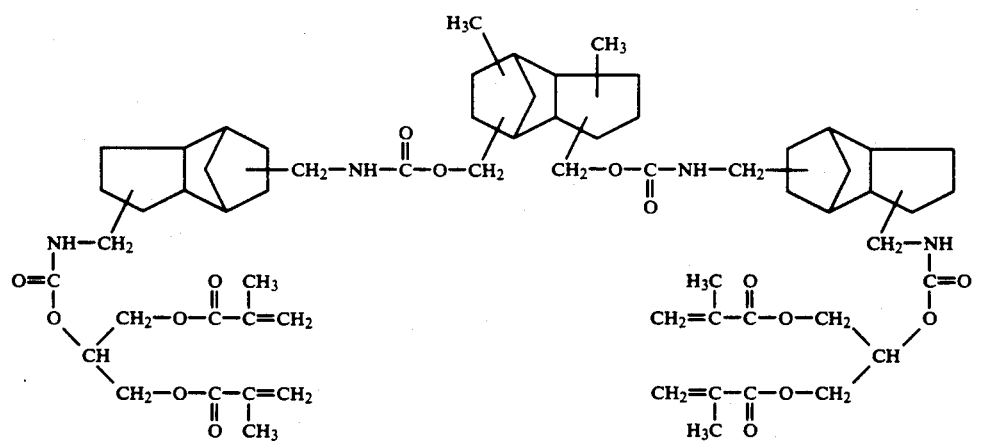
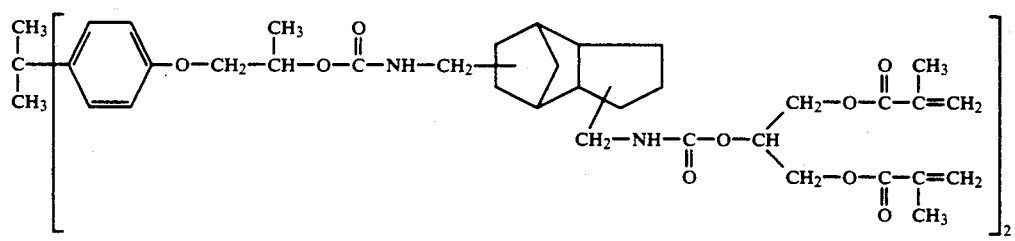
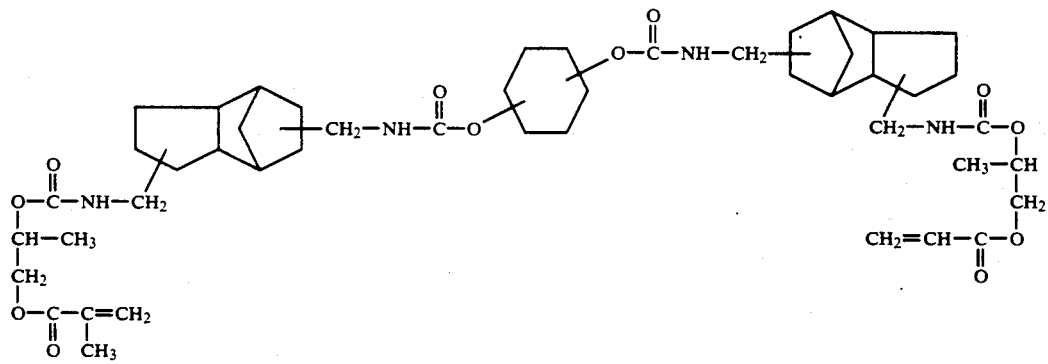
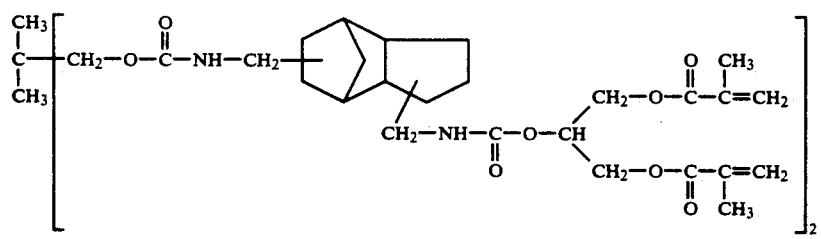
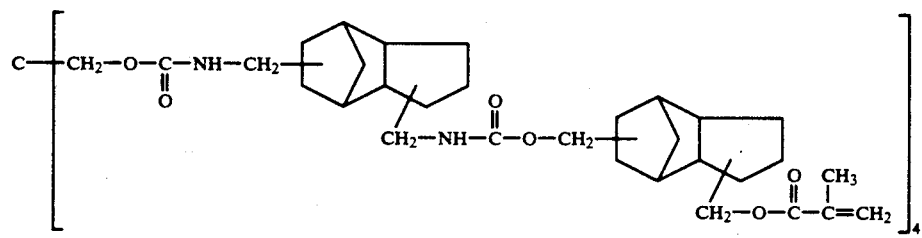

-continued
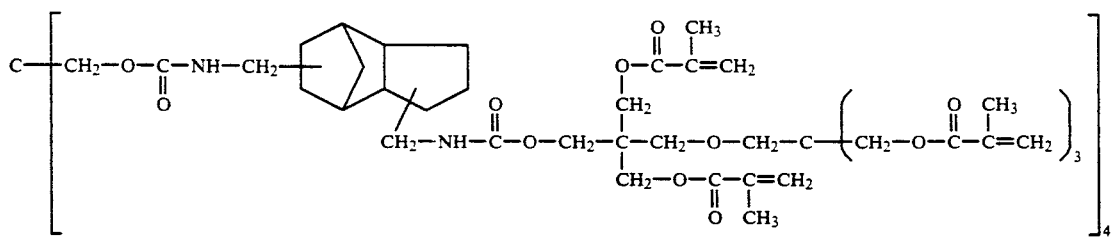
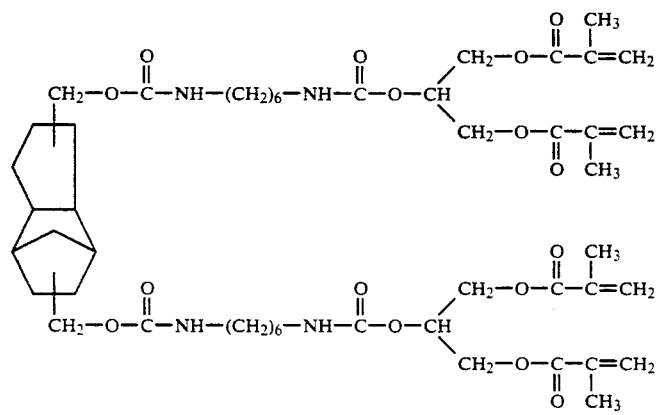
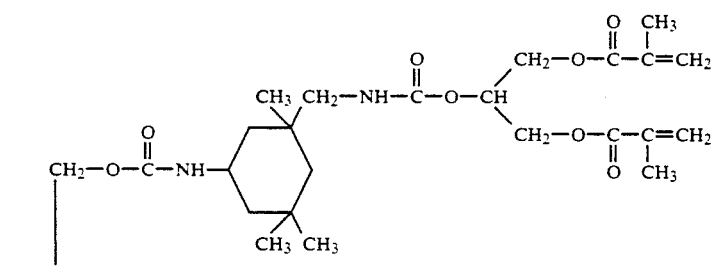
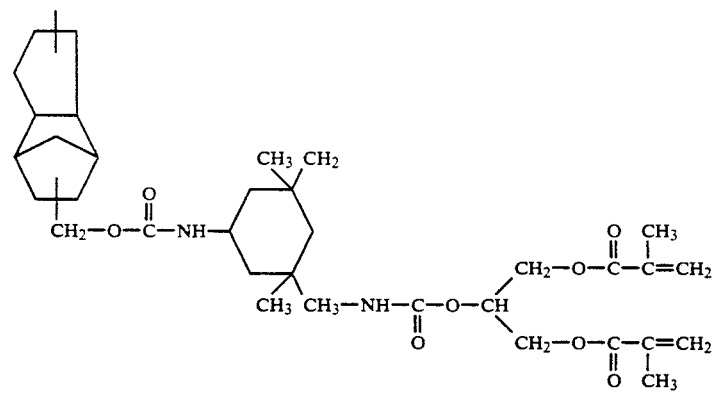
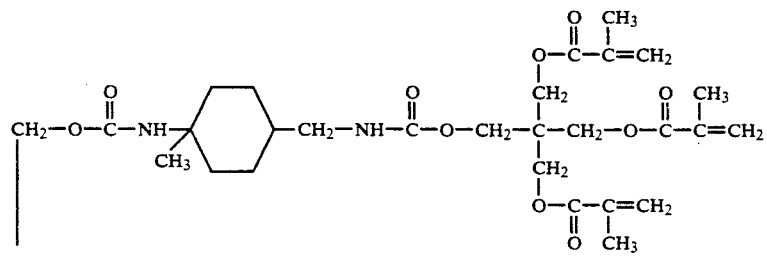

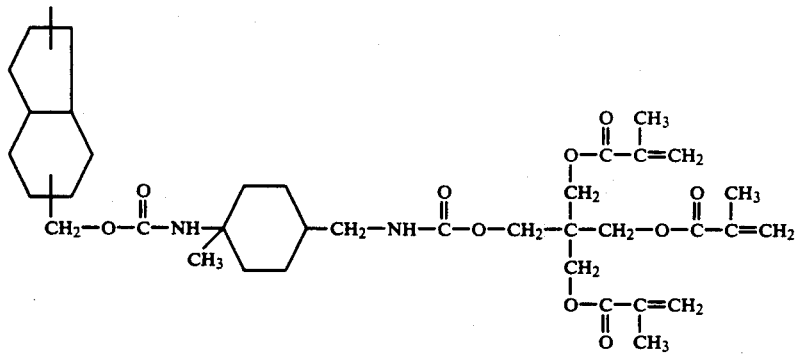

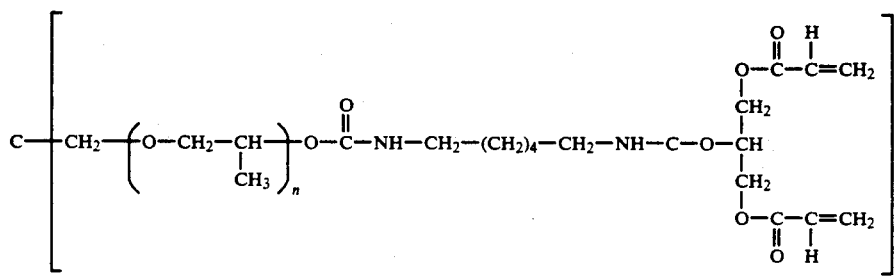

n = 1.225 (statistical mean value for 4 chains)

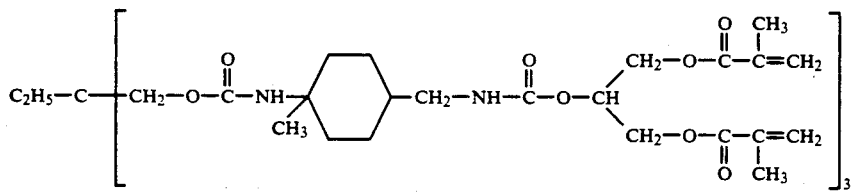

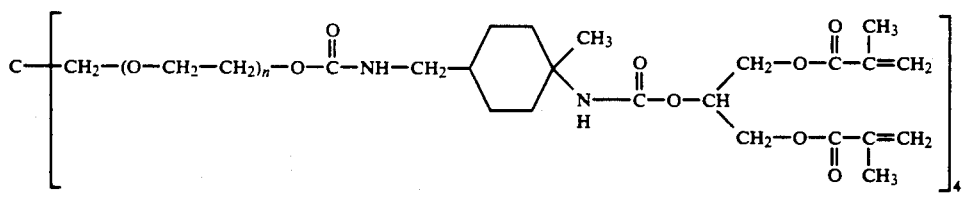

n = 1.225 (statistical mean value for 4 chains)

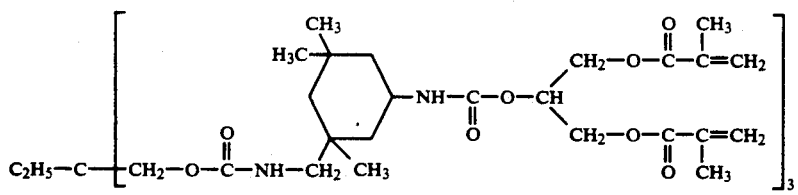

So-called bis-GMA of the formula

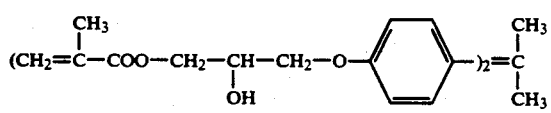

is particularly preferred as the monomer.

It is of course possible to use mixtures of various (meth)-acrylic acid esters which can form crosslinkages. Mixtures of 20 to 70 parts by weight of bis-GMA- and 30 to 80 parts by weight of triethylene glycol dimethacrylate may be mentioned as examples.

Component (c)

(Meth)-acrylic acid esters which cannot form crosslinkages are in general monofunctional (meth)-acrylates. Examples which may be mentioned are $C_1-C_{12}$-, preferably $C_1-C_4$-alkyl methacrylates, such as methyl methacrylate, ethyl methacrylate, n-propyl methacrylate, i-propyl methacrylate, n-butyl methacrylate and tert.-butyl methacrylate, hydroxyalkyl methacrylates, such as 2-hydroxyethyl methacrylate, 2-hydroxypropyl methacrylate, diethylene glycol monomethacrylate and triethylene glycol monomethylmethacrylate, and alkoxyalkyl methacrylates, such as 2-methoxyethyl methacrylate, 3-methoxybutyl methacrylate and ethyl triglycol methacrylate.

Preferred (meth)-acrylic acid esters which cannot form crosslinkages are methyl methacrylate, ethylene metharcylate and hydroxyethyl methacrylate.

In general, a mixture of components (b) and (c) is employed as the monomer mixture for the dental materials according to the invention. These mixtures preferably have a viscosity in the range from 50 to 5,000 mPa.s, preferably in the range from 100 to 2,000 mPa.s (in each case at 20° C.).

Component (d)

The dental materials according to the invention can contain additives which are known per se. Additives which may be mentioned are starter additives, stabilizers, fillers, pigments, dyestuffs, light stabilizers, fluorescent agents or plasticizers.

Starter additives which can be used for initiating the polymerization are starter systems which are known per se (literature Houben Weyl, Methoden der organischen Chemie (Methods of Organic Chemistry) Volume E20, page 15 et seq., Georg Thieme Verlay, Stuttgart 1987). These are systems which supply free radicals, anions or cations and can initiate free radical, anionic or cationic polymerization. In the case of systems which supply free radicals, peroxides or aliphatic azo compounds, for example benzoyl peroxide, lauryl peroxide or azoisobutyrodinitrile, are particularly suitable; the systems are usually employed in amounts of 0.1 to 5% by weight. While hardening at elevated temperature can be carried out merely by means of peroxides or other free radical starters, it is generally advantageous to add accelerators, preferably aromatic amines, for hardening at room temperature. Suitable accelerators are, for example, N,N-substituted toluidines and xylidines, such as N,N-dimethyl-p-toluidine or N,N-bis-(2-hydroxyethyl)-xylidine. Hardening can in general be achieved by addition of 0.5 to 3% by weight of the amines mentioned.

However, it is also possible to prepare dental materials which polymerize under the action of light, for example UV light, visible light or laser light. In these cases, photopolymerization initiators and accelerators are employed.

Photopolymerization initiators are known per se (literature: Houben Weyl, Methoden der organischen Chemie (Methods of Organic Chemistry), Volume E20, page 80 et seq., Georg Thieme Verlag Stuttgart 1987). They are preferably carbonyl compounds, such as benzoin and derivatives thereof, in particular benzoin methyl ether, benzyl and benzyl derivatives, for example 4,4-oxidibenzyl, and other dicarbonyl compounds, such as thiacetyl, 2,3-pentadione or metal carbonyls, such as pentacarbonyl-manganese, and quinones, such as 9,10-phenanthrenequinone and camphorquinone or derivatives thereof.

The content of such photopolymerization initiators is preferably about 0.01 to about 5% by weight of the total composition.

The photopolymerizable compositions which can be hardened by means of light preferably also contain substances which accelerate the polymerization reaction in the presence of photopolmerization initiators. Known accelerators are, for example, aromatic amines, such as p-toluidine and dimethyl-p-toluidine, trialkylamines, such as trihexylamine, polyamines, such as N,N,N',N'-tetraalkylalkylenediamine, barbituric acid and dialkylbarbituric acid, and sulphimides.

The accelerators are in general employed in an amount of 0.01 to about 5% by weight of the total mixture.

It is also possible to add UV-stabilizers to the dental materials according to the invention in order to avoid subsequent darkening during ageing.

A particularly suitable UV stabilizer is 2-hydroxy-4-methoxybenzophenone. Another preferred material is 2-(2'-hydroxy-5-methylphenyl)-benzotriazole. Hydroquinone, p-benzoquinone and p-butylhydroxytoluene may also be mentioned as examples.

The dental materials according to the invention can also contain pigments and dyestuffs which are known per se to establish a color which is as true to nature possible.

Preferred dental materials according to the invention contain a) 5 to 35 parts by weight of a filler containing polymeric crosslinked (meth)-acrylates having a particle size in the range from 0.001 to 100 μm, a degree of swelling of 100 to 2,000% by weight and a degree of crosslinking of 1 to 100% by weight, in each case based on the polymer, b) 40 to 90 parts be weight of (meth)-acrylates which can form crosslinkages, c) 0 to 40 parts by weight of (meth)-acrylates which cannot form crosslinkages and d) 0.1 to 10 parts by weight of one or more additives.

Dental materials containing a) 10 to 30 parts by weight of a filler containing polymeric crosslinked (meth)-acrylates having a particle size in the range from 0.001 to 100 μm, a degree of swelling of 100 to 2,000% by weight and a degree of crosslinking of 1 to 100% by weight, in each case based on the polymer, b) 50 to 90 parts by weight of (meth)-acrylates which can form crosslinkages, c) 0 to 40 parts by weight of (meth)-acrylates which cannot form crosslinkages and d) 0.1 to 10 parts by weight of one or more additives, are particularly preferred.

A process has also been found for the preparation of the dental materials according to the invention, which is characterized in that a mixture of a) 5 to 35 parts by weight of a filler consisting of polymeric crosslinked (meth)-acrylates having a particle size in the range from 0.001 to 10 μm, a degree of swelling of 100 to 2,000% by weight and a degree of crosslinking of 1 to 100% by weight, in each case based on the polymer, b) 40 to 90 parts by weight of (meth)-acrylates which can form crosslinkages, c) 0 to 40 parts be weight of (meth)-acrylates which cannot form crosslinkages and d) 0.1 to 10 parts by weight of additives, is polymerized.

The polymerization is in general carried out under the abovementioned conditions.

The dental materials according to the invention can be processed by shaping to give false teeth and dental prostheses, such as crowns, bridges, inlays and onlays, and to dental fillings and dental lacquers. The polymerized dental materials according to the invention are distinguished by a favorable combination of properties. They have a marked hardness, a high rigidity and a high resistance to abrasion, coupled with good toughness. They can easily be colored and can be adjusted to the natural tooth color.

EXAMPLE 1

Preparation of a polymethacrylic acid ester of ethylene glycol dimethacrylate 1,800 g of butan-2-one, 200 g of ethylene glycol dimethacrylate and 2 g of dibenzoyl peroxide are weighed into a 3 liter glass reactor fitted with a blade stirrer, reflux condenser, internal thermometer, gas inlet and gas outlet tube. The mixture is heated under reflux for 2 hours, while stirring at 300 revolutions per minute and flushing with nitrogen. An easily stirrable suspension results. 190 g of fine powder can be obtained from this by spray drying. The average particle size (measured by laser correlation spectroscopy) is 700 nm, the gel content is 98.4% and the degree of swelling (measured in tetrahydrofuran) is 310%.

EXAMPLE 2

Preparation of a polymethacrylic acid ester from glycerol dimethacrylate 500 g of glycerol dimethacrylate and 5 g of dibenzoyl peroxide were reacted in 2,000 g of butan-2-one in accordance with the procedure described in Example 1. 475 g of powder having a particle size of 350 nm, a gel content of 97.3% and a degree of selling of 280% are obtained.

EXAMPLE 3

Polymerizable composition 104 g of polymer from Example 1, 248 g of bis-GMA, 152 g of triethylene glycol dimethacrylate and 2.1 g of dibenzoyl peroxide are kneaded in a laboratory kneader in the course of 30 minutes. The resulting composition is stored at 35° C. for 5 hours. A transparent, non-tacky, dough-like paste is obtained.

EXAMPLE 4

Polymerizable composition 36 g of polymer from Example 2, 120 g of the reaction product of 2,2,4-trimethylhexamethylene diisocyanate and 2 mol of 2-hydroxyethyl methacrtylate [1,6-bis-(methacryloyloxyethoxycarbonylamino)-2,2,4-trimethylhexane] and 0.64 g of dibenzoyl peroxide are kneaded to a composition as described in Example 3.

EXAMPLE 5

20 g of polymer from Example 2, 60 g of bis-GMA, 30 g of triethylene glycol dimethacrylate, 10 g of 4-methoxybutyl methacrylate and 0.5 g of dibenzoyl peroxide are kneaded to a composition as described in Example 3.

EXAMPLE 6

The compositions from Examples 3, 4 and 5 and two comparison materials were polymerized at 140° C. under 200 bar in the course of 10 minutes to give a test sheet. Values of the flexural strength according to DIN 13 922 and the flexural E modulus according to DIN 13 922, and the penetration depth according to Wallace were determined.

The Wallace method is used to determine the impression hardness of plastics. A Vickers diamond is applied to the surface under a preload of 1 p and is then subjected to a main load of 100 p for 60 seconds. The penetration depth of the diamond under the main load is measured as a measure of the penetration resistance. In contrast to the Vickers or Brinell hardness measurements, in which the test force if related to the dimensions of the impression which remains, the Wallace method records the elastic and permanent deformation of the plastic.

| | Flexural Strength $N/nm^2$ | E modulus $N/nm^2$ | HW $\mu m$ |
|---|---|---|---|
| Example 3 | 140 ± 7 | 3800 ± 150 | 16.2 ± 0.9 |
| Example 4 | 136.1 ± 11 | 4100 ± 70 | 15.8 ± 0.5 |
| Example 5 | 132 ± 10 | 3850 ± 130 | 17.0 ± 0.6 |
| customary PMMA system | 112 ± 9 | 2800 ± 100 | 22.8 ± 1.5 |
| WO 82/02556 Example 1 | 118 ± 10 | 3050 ± 80 | 20.3 ± 1.1 |

It will be appreciated that the instant specification and claims are set forth by way of illustration and not limitation, and that various modifications and changes may be made without departing from the spirit and scope of the present invention.

What is claimed is:

1. A composition suitable for forming a dental component, consisting essentially of methacrylates and from 0.1 to 10 parts by weight of one or more additives, the methacrylates consisting essentially of about (a) 5 to 35 parts of a filler comprising a polymeric crosslinked (meth)-acrtylate having a particle size of about 0.01 to 10 μm, a degree of swelling of about 100 to 2,000% by weight and a degree of crosslinking of about 50 to 100% by weight, in each case based on the polymer, and (b) 40 to 90 parts of a (meth)-acrylate which can form crosslinkages.

2. A composition according to claim 1, wherein the filler has a gel content of about 90 to 100% by weight.

3. A composition according to claim 1, wherein the filler has an active surface area of about 20 to 600 $m^2/g$.

4. A composition according to claim 1, wherein (b) has a viscosity of about 50 to 5,000 mPa.s.

5. A composition according to claim 4, wherein the filler has a gel content of about 90 to 100% by weight.

* * * * *

UNITED STATES PATENT AND TRADEMARK OFFICE
CERTIFICATE OF CORRECTION

PATENT NO. : 5,147,903

DATED : September 15, 1992

INVENTOR(S) : PODSZUN et al

It is certified that error appears in the above-identified patent and that said Letters Patent is hereby corrected as shown below:

Col. 24 line 44   Delete " acrtylate " and substitute -- acrylate --

Signed and Sealed this

Fifteenth Day of March, 1994

Attest:

BRUCE LEHMAN

Attesting Officer

Commissioner of Patents and Trademarks